(12) United States Patent
Bacher et al.

(10) Patent No.: US 7,402,408 B2
(45) Date of Patent: Jul. 22, 2008

(54) ASSAY FOR INHIBITORS OF ISPH

(75) Inventors: Adelbert Bacher, Garching (DE); Petra Adam, Kramsach (AT); Wolfgang Eisenreich, Garching (DE); Tobias Gräwert, Augsburg (DE); Stefan Hecht, Bad Aibling (DE); Felix Rohdich, Zolling (DE); Ferdinand Zepeck, München (DE)

(73) Assignee: Adelbert Bacher, Garching (DE)

( * ) Notice: Subject to any disclaimer, the term of this patent is extended or adjusted under 35 U.S.C. 154(b) by 282 days.

(21) Appl. No.: 10/543,076

(22) PCT Filed: Jan. 15, 2004

(86) PCT No.: PCT/EP2004/000264

§ 371 (c)(1),
(2), (4) Date: Sep. 2, 2005

(87) PCT Pub. No.: WO2004/065623

PCT Pub. Date: Aug. 5, 2004

(65) Prior Publication Data

US 2006/0099668 A1    May 11, 2006

(30) Foreign Application Priority Data

Jan. 22, 2003   (DE) ................................ 103 02 370

(51) Int. Cl.
*C12Q 1/26* (2006.01)
(52) U.S. Cl. ....................................................... 435/25
(58) Field of Classification Search ........................ None
See application file for complete search history.

(56) References Cited

FOREIGN PATENT DOCUMENTS

WO    WO-02/083720    10/2002
WO    WO-2004/035810  4/2004

OTHER PUBLICATIONS

Ollagnier, S. et al., "Activation Of The Anaerobic Ribonucleotide Reductase From *Escherichia coli*, The Essential Role Of The Iron-Sulfur Center For *S*-Adenosylmethionine Reduction", The Journal of Biological Chemistry 272 (39) (1997), pp. 24216-24223.
Adam, P. et al., "Biosynthesis Of Terpenes: Studies On 1-hydroxy-2-methyl-2-(E)-butenyl 4-diphosphate Reductase", Proceedings of The National Academy of Sciences of the United States of America, 99 (19) Sep. 17, 2002, pp. 12108-12113.
Altincicek, B. et al., "LytB Protein Catalyzes The Terminal Step Of The 2-*C*-methyl-D-erythritol-4-phosphate Pathway Of Isoprenoid Biosynthesis", FEBS Letters 532 (2002), pp. 437-440.
Rohdich, F., et al. "The Deoxyxylose Phosphate Pathway of Isoprenoid Biosynthesis: Studies on the Mechanisms of the Reactions Catalyzed by IspG and IspH protein," PNAS, vol. 100, No. 4, 2003, pp. 1586-1591.

*Primary Examiner*—Jon P Weber
*Assistant Examiner*—Bin Shen
(74) *Attorney, Agent, or Firm*—Connolly Bove Lodge & Hutz LLP

(57) ABSTRACT

Assay for testing a sample for the presence or absence of inhibition of the enzymatic conversion of 1-hydroxy-2-methyl-(E)-butenyl 4-diphosphate into isopentenyl diphosphate and/or dimethylallyl diphosphate by the following steps: (a) reacting an aqueous mixture containing 1-hydroxy-2-methyl-(E)-butenyl 4-diphosphate, a 1-hydroxy-2-methyl-(E)-butenyl 4-diphosphnte reductase, and a reducing agent under predetermined reaction conditions for a predetermined period of time; (b) analyzing the reaction mixture obtained in step (a) for the consumed amount of 1-hydroxy-2-methyl-(E)-butenyl 4-diphosphate and/or NAD(P)H and/or for the produced amount of isopentenyl diphosphate, and/or dimethylallyl diphosphate and/or NAD(P)$^+$; (c) repeating step (a) in the presence of the sample to be tested; (d) repeating step (b) with the reaction mixture defined in step (c); (e) comparing the results of steps (b) and (d).

10 Claims, 1 Drawing Sheet

Prior Art

SEQUENCE LISTING

<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: PCR primer

<400> SEQUENCE: 1
tggaggggat ccatgcagat cctgttggcc acc         33

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2

```
gcatttctgc agaacttagg c                                              21

<210> SEQ ID NO 3
<211> LENGTH: 37
<212> TYPE: DNA
<213> ORGANISM: Artificial Sequence
<220> FEATURE:
<223> OTHER INFORMATION: PCR primer

<400> SEQUENCE: 3
gtcagtggat ccatggctat cactggcatc tttttcg                             37

<210> SEQ ID NO 4
<211> LENGTH: 31
<212> TYPE: DNA
<213> ORGANISM: Artificial Sequence
<220> FEATURE:
<223> OTHER INFORMATION: PCR primer

<400> SEQUENCE: 4
ggagctctgc agtcaggcat tgagaatttc g                                   31

<210> SEQ ID NO 5
<211> LENGTH: 33
<212> TYPE: DNA
<213> ORGANISM: Artificial Sequence
<220> FEATURE:
<223> OTHER INFORMATION: PCR primer

<400> SEQUENCE: 5
ggtctgggat ccatggctga ttgggtaaca ggc                                 33

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
gttcagctgc agttaccagt aatgctccgc                                     30
```

ASSAY FOR INHIBITORS OF ISPH

RELATED APPLICATIONS

Figure 1:
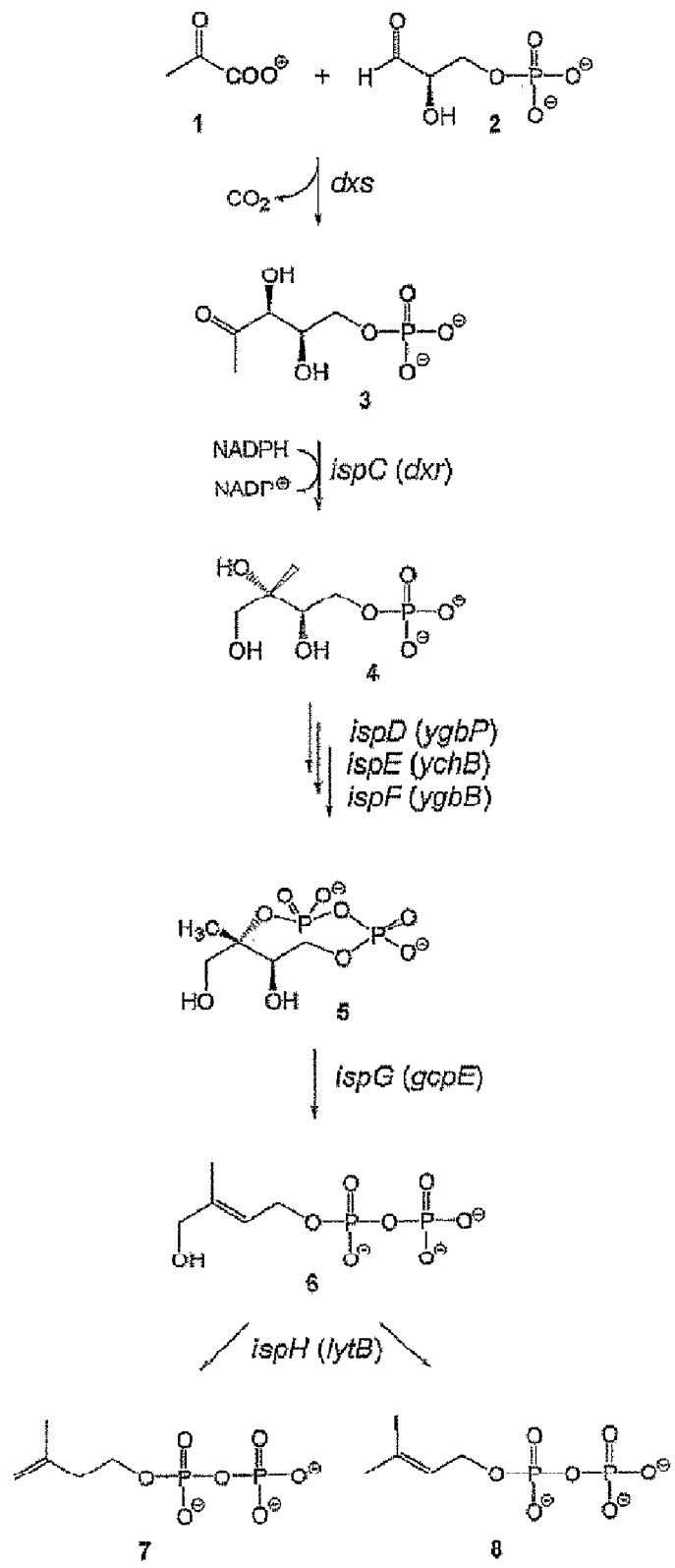

This application is a national stage application (under 35 U.S.C. 371) of PCT/EP2004/0002∝filed Jan. 15, 2004 which claims benefit to German application 103 02 370.4 filed Jan. 22, 2003.

For a period of several decades, the mevalonate pathway has been considered as the unique source for the universal terpene precursors, isopentenyl diphosphate (IPP; 7) and dimethylallyl diphosphate (DMAPP; 8) (FIG. 1). The pioneering studies on this pathway by Bloch, Comforth, Lynen and their coworkers (for review see Refs. 1-4) served as the basis for the development of cholesterol biosynthesis inhibitors which have a central role in the prevention and treatment of cardiovascular disease.

Only about a decade ago, independent work by Arigoni, Rohmer and their respective coworkers proved the existence of a second isoprenoid pathway which is operative in many eubacteria and in the plastid compartment of higher plants (for review see Refs. 5-7). Subsequent studies demonstrated that Dxs protein catalyzes the condensation of pyruvate (1) with D-glyceraldehyde 3-phosphate (2) affording 1-deoxy-D-xylulose 5-phosphate (3) (8, 9) which is transformed into 2Cmethyl-D-erythritol 4-phosphate (4) by a skeletal rearrangement and reduction catalyzed by the IspC protein (FIG. 1) (10). This polyol phosphate is then converted into 2C-methyl-D-erythritol 2,4-cyclodiphosphate (5) by the consecutive action of the IspD, IspE and IspF proteins (11-13; for review see Ref. 14).

A recombinant *Escherichia coli* strain engineered for expression of the xylB and ispCDEF genes was shown to transform exogenous $^{13}$C-labeled 1-deoxy-D-xylulose to the endogenous cyclic diphosphate 5 in high yield (15). The additional operation of a recombinant ispG gene resulted in the in vivo formation of 1-hydroxy-2-methyl-2-(E)-butenyl 4-diphosphate (6) (15) which was also isolated from an ispH-deficient *E. coli* mutant (16). Subsequently, the in vitro formation of 6 from 5 by crude cell extracts of *E. coli* overexpressing ispG was confirmed by radiochemical methods (17). 6 was shown by in vivo as well in vitro experiments to serve as the biosynthetic precursor of IPP (7) and DMAPP (8) which were obtained in a ratio of 6:1 by the catalytic action of the IspH protein (18, 19).

For numerous pathogenic eubacteria as well as for the malaria parasite *P. falciparum*, the enzymes involved in the non-mevalonate pathway are essential. The intermediates of the mevalonate-independent pathway cannot be assimilated from the environment by pathogenic eubacteria and *P. falciparum*. The enzymes of the alternative isoprenoid pathway do not occur in mammalia which synthesize their isoprenoids and terpenoids exclusively via the mevalonate pathway. Moreover, the idiosyncratic nature of the reactions in this pathway reduces the risk of cross-inhibitions with other, notably mammalian enzymes.

Therefore, enzymes of the alternative isoprenoid pathway seem to be specially suited as targets for novel agents against pathogenic microorganisms and herbicides. The identification of these targets, e.g. genes and cognate enzymes of these pathways is obligatory for this purpose. In order to be able to use a target enzyme in an assay for inhibitors, a substrate, any co-proteins, co-factors or co-substrates of that enzyme have to be known. Up to now, the IspH enzyme could not be used for screening for inhibitors of the enzymatic conversion of 1-hydroxy-2-methyl-(E)-butenyl 4-diphosphate into isopentenyl diphosphate and/or dimethylallyl diphosphate, since the co-substrate capable of providing this enzyme with the necessary reducing equivalents for said conversion have remained unknown.

BREIF SUMMARY OF THE INVENTION

It is therefore the problem of this invention to provide an assay for efficiently screening samples for the presence or absence of inhibition of the enzymatic conversion of 1-hydroxy-2-methyl-(E)-butenyl 4-diphosphate into isopentenyl diphosphate and/or dimethylallyl diphosphate. This problem is solved by the assay of claim 1 and 2. Preferred embodiments are defined in the subclaims.

The present invention is based on the surprising finding of reducing agents (notably flavodoxin) that act efficiently as electron shuttle to provide the 1-hydroxy-2-methyl-(E)-butenyl 4-diphosphate reductase (e.g. IspH) with the electrons necessary for the enzymatic conversion of 1-hydroxy-2-methyl-(E)-butenyl 4-diphosphate into isopentenyl diphosphate and/or dimethylallyl diphosphate. In step (a) of the assay of the invention, the assay mixture may therefore contain a flavodoxin or a function-conservative variant thereof. Flavodoxin reductase or a function-conservative variant thereof may be used to reduce and recycle flavodoxin. NAD(P)H may be used as a reservoir for reducing equivalents due to its capability to act as reducing substrate of flavodoxin reductase.

BREIF DESCRIPTION OF THE DRAWINGS

FIG. 1 shows the non-mevalonate isoprenoid pathway or alternative isoprenoid pathway.

DETAILED DESCRIPTION OF THE INVENTION

As the 1-hydroxy-2-methyl-(E)-butenyl 4diphosphate reductase the IspH enzyme or a function-conservative variant thereof is preferably used. The gene of the IspH enzyme used in the assay of the invention may be derived from any organism having the non-mevalonate isoprenoid pathway, like plants, eubacteria or *Plasmodium*. An example of a source of the ispH gene is *E. coli*. Sequence information and information on cloning and expressing ispH is known from WO02/83720. Variants (e.g. mutants, truncated forms, or genes of fusion proteins comprising the IspH enzyme) may be used provided said variations do not abolish the enzymatic activity of the IspH enzyme for said enzymatic conversion. The IspH enzyme may be produced by recombinant expression of the ispH gene in a suitable host according to general methods of molecular biology. A preferred host is *E. coli*. Preferably, the expressed IspH enzyme is purified. For this purpose, IspH is preferably expressed as a fusion protein with a tag allowing purification of the fusion protein by affinity chromatography. Examples of such tags are glutathion reductase, maltose binding protein, or a 6×His-tag. A fusion of the IspH enzyme with maltose binding protein proved to be advantageous in terms of ease of purification and in terms of preserving the IspH enzyme in an active state. However, fusions with other tags allowing easy purification may also be used provided these other tags do not interfere with the assay of the invention. Most preferably, the IspH enzyme is produced and purified as described in Examples 1 to 3. It is preferred to use an IspH enzyme from an organism related to the target organism of a prospective inhibitor (i.e. from an organism to be combatted with an antibiotic containing the inhibitor identified according to the invention).

Said reducing agent may be any reductant capable of providing 1-hydroxy-2-methyl-(E)-butenyl 4-diphosphate reductase with the reducing equivalents required for said enzymatic conversion. Said reducing agent may be a small-molecular compound (e.g. a viologen like methylviologen or a deazaflavin derivative like 10-methyl-5-deaza-isoalloxazine plus light) or a polymeric compound like a protein, notably a redox protein. Preferably, a redox protein is used as said reducing agent. Examples of such redox proteins are flavodoxin, ferredoxin, glutharedoxin, or thioredoxin. The most preferred reducing agent is flavodoxin. Naturally, said redox protein has to be provided in its reduced form. A redox protein (in its reduced form) may be used in amounts sufficient to support multiple turnover cycles of said 1-hydroxy-2-methyl-(E)-butenyl 4-diphosphate reductase. Alternatively, said redox protein may be used in comparable molar amounts as said 1-hydroxy-2-methyl-(E)-butenyl 4-diphosphate reductase. In this latter case, however, a system capable of recycling the reduced form of said redox protein is preferably employed. An important example of such a recycling system is flavodoxin reductase/NAD(P)H which is most preferably used together with flavodoxin as said reducing agent.

Flavodoxin may be produced as described in Examples 4 and 6. Alternatively, it may be obtained from a commercial source. Preferably, one uses flavodoxin from an organism related to the organism from which the 1-hydroxy-2-methyl-(E)-butenyl 4-diphosphate reductase is derived. Most preferably, flavodoxin and IspH derive from the same organism, e.g both from E. coli. Function-conservative variants of flavodoxin may be any mutated or truncated version provided it is capable of functioning as electron shuttle between the IspH enzyme and flavodoxin reductase. This capability can be determined easily by experiment, e.g. using the assay of Example 8 and comparison with the flavodoxin of Example 4.

Flavodoxin reductase may be produced according to examples 5 and 7 or be obtained commercially. Function-conservative variants of flavodoxin reductase may be used similary as described for flavodoxin. Flavodoxin and flavodoxin reductase should derive from related or, preferably, from the same organism in order to guarantee that said flavodoxin may be reduced well by said flavodoxin reductase.

As NAD(P)H, NADPH or NADH is used both of which are commercially available from generally-known sources. NADPH is preferred over NADH, since flavodoxin reductase is more active with NADPH than with NADH. Instead of NAD(P)H, NAD(P)$^+$ may be used in the assay of the invention together with a system capable of reducing NAD(P)$^+$ to NAD(P)H. Various enzymatic system are known that can reduce NAD(P)$^+$ to NAD(P)H. Examples are alcohol dehydrogenase, glucose dehydrogenase, and lactate dehydrogenase.

1-hydroxy-2-methyl-(E)-butenyl 4-diphosphate and various isotopically-labelled forms thereof are amenable as described by Hecht et al. (20) and in WO02/83720.

The assay of the invention is preferably carried out in an aqueous buffer. The pH of the buffer should be in a range where the involved enzymes are sufficiently active. Preferably, the pH is in the rage between 7 and 9, more preferably between 7 and 8. The temperature of the assay may be in the range between 5 and 50° C., preferably between 15 and 40° C. 37° C. is most preferred. The assay buffer preferably contains a sulfhydryl reagent like dithiothreitol (DTT) in a concentration of e.g 0.5 to 5 mM. The assay of the invention may be carried out under aerobic or under anaerobic conditions. Under anaerobic conditions, higher rates of said enzymatic conversion may be obtained with IspH. The assay reaction may be started by the addition of any one of the essential compounds given in item (a) of claim 1 or 2. Preferably, the reaction is started by the addition of 1-hydroxy-2-methyl-(E)-butenyl 4-diphosphate or 1-hydroxy-2-methyl-(E)-butenyl 4-diphosphate reductase.

For increasing the activity of the 1-hydroxy-2-methyl-(E)-butenyl 4-diphosphate reductase, the assay mixtures may further contain small concentrations of a divalent metal ion, notably a transition metal ion, like $Ni^{2+}$, $Co^{2+}$, $Mn^{2+}$, $Fe^{2+}$, $Cu^{2+}$, or $Zn^{2+}$. $Co^{2+}$ is preferred. Said concentration may be between 0.1 to 5 mM, preferably 0.5 to 2 mM.

In the screening assay of the invention, the enzymatic conversion of 1-hydroxy-2-methyl-(E)-butenyl 4-diphosphate to isopentenyl diphosphate and/or dimethylallyl diphosphate is followed in the absence and in the presence of a sample to be tested for inhibition of said enzymatic conversion. If said conversion is slower in the presence of said sample under otherwise identical conditions, said sample is an inhibitor of said conversion. Progress of said enzymatic conversion may be followed by consumption of 1-hydroxy-2-methyl-(E)-butenyl 4-diphosphate, formation of isopentenyl diphosphate and/or dimethylallyl diphosphate, or consumption of said reducing agent. If a redox protein is used as said reducing agent, consumption of a component of said system capable of recycling the reduced form of said redox protein may be followed. If flavodoxin reductase/NAD(P)H is used as said recycling system, consumption of NAD(P)H is used. Alternatively, formation of NAD(P)$^+$ may be followed. Consumption or formation of 1-hydroxy-2-methyl-(E)-butenyl 4-diphosphate, isopentenyl diphosphate and dimethylallyl diphosphate may be quantitated by HPLC combined with a uv-absorbance detector or, preferably, a scintillation detector. Consumption of NAD(P)H or formation of NAD(P)$^+$ may be followed photometrically around 340 nm.

Said conversion may be followed continuously or in intervals. Alternatively, the reaction may be run for a predetermined period of time of e.g several minutes, stopped after said predetermined period of time, and then analysed by one of the methods mentioned above. HPLC analysis is most suited to follow the conversion in intervals by taking HPLC samples at predefined intervals from the reaction mixture or for a final analysis after the reaction has been stopped. The reaction may be stopped after a predetermined period of time. This period of time may e.g. be between 1 minute to 1 hour, preferably 2 minutes to 15 minutes. For continuously following said conversion, the characteristic 340 nm absorbance of NADH is preferably made use of.

The assay of the invention may be performed at low scale, i.e. with a small number of samples to be tested. The assay of the invention may also be performed on a large scale, i.e. with many samples to be tested. Said assay can easily be automated such that many samples can be assayed in parallel. Using the assay of the invention, high-throughput screening for inhibitors of said enzymatic conversion can be carried out. If many samples to be tested are analysed in parallel, the assay are preferably carried out in multi-well plates like 24-, 96- or 256-well plates and the reactions are preferably followed photometrically at 340 nm. On a multi-well plate, one or a small number of wells where said conversion is followed in the absence of a sample to be tested may be sufficient, whereas in the majority of wells said conversion is followed in the presence of different samples to be tested.

Samples to be tested for inhibition of said conversion may e.g. be specifically selected compounds surmised to be inhibitors like substrate analogues. For making full use of the potential of the invention, large collections of compounds are screened like combinatorial libraries. Such libraries may be peptide libraries or other libraries of organic chemical compounds. Many such libraries are commercially available.

Typically, a sample tested positive in the assay of the invention is then validated. Validation may comprise testing a sample that was tested positive in the assay of the invention for inhibition of flavodoxin reductase or for inhibition of electron shuttling from NAD(P)H to flavodoxin. This may e.g. be done by using an artificial unspecific reductant like a viologen (e.g. methylviologen) or a deazaflavin derivative/light instead of the flavodoxin/flavodoxin reductase system. A positive sample preferably inhibits said 1-hydroxy-2-methyl-(E)-butenyl 4-diphosphate reductase also if tested with said artificial unspecific reductant.

An inhibitor of 1-hydroxy-2-methyl-(E)-butenyl 4-diphosphate reductase identified using the assay of the invention may be used as or developed to a drug for combatting organisms having the non-mevalonate isoprenoid pathway, notably bacteria or *Plasmodium*. Since humans do not have said pathway, drugs may be developed having little side-effects in humans. An inhibitor found in the assay of the invention may of course be optimised for use as a drug. Thus, such an inhibitor may function as a lead compound (or lead structure) for developing pharmaceuticals. Said optimisation may comprise exchange or addition of chemical groups for adjusting the pharmacokinetic and pharmacodynamic properties of such an inhibitor or lead compound. Said optimisation may be performed by known methods of medicinal chemistry and pharmacology.

EXAMPLES

Example 1

Cloning and Expression of the ispH Gene of *Escherichia coli* as Maltose Binding Fusion Protein (MalE/IspH)

The ispH gene of *E. coli* (formerly designated IytB; GenBank accession number AY062212) is amplified by PCR using chromosomal *E. coil* DNA as template and the oligonucleotides IytBvo and IytBhi (Table 1) as primers. The amplificate is purified, treated with the restriction enzymes BamHI and PstI, and ligated into the expression vector pMALC2 (New England Biolabs) which has been treated with the same enzymes. The resulting plasmid pMALispH is electrotransformed into the *E. coli* strain B ER2566 (New England Biolabs, 21) affording the recombinant strain BL21-pMALispH, respectively.

Example 2

Production of *E. coli* Cell Mass

The *E. coli* strain BL21-pMALispH, respectively is grown in minimal medium M9 (22) using a 2 I fermenter (BioFlo3000, New Brunswick Scientific). The autoclaved culture medium containing sodium D,L-lactate (1.3 g/l) is cooled to 37° C. Ampicillin (180 mg/l), FeCl3 (30 mg/l), MgCl2 (375 mg/l) and CaCl2 (225 mg/l) are added and the pH was adjusted to 7.0. The medium is inoculated with an overnight culture of the recombinant *E. coli* strain at a ratio of 1:100. The cultures are incubated at 37° C. with variable agitation of 300-1000 rpm, and the pH is adjusted to 7.0 at regular intervals by addition of 6 M hydrochloric acid. The relative oxygen saturation is maintained at 30% via the stirrer speed. After reaching an oxygen saturation of 30%, sodium D,L-lactate, ammonium chloride and ammonium sulfate (1.3:0.1:0.05 (w/w)) are added continuously between a range of 30.5 and 50.0% oxygen saturation by a pulse feed program. At an optical density (600 nm) of 20, IPTG is added to a final concentration of 1.5 mM, and incubation is continued for 4 h. Cells are harvested by centrifugation, washed with 0.9 (w/v) sodium chloride and stored at −20° C.

Example 3

Purification of Recombinant MalE/IspH Fusion Protein

Frozen cell mass (3.5 g) *E. coli* BL21-pMALispH is thawed in 35 ml of 50 mM Tris-hydrochloride, pH 8.0, containing 0.2 M sodium chloride (buffer A). The suspension is subjected to ultrasonic treatment and centrifuged. The supernatant is applied to a column of amylose resin FF (Amersham Pharmacia Biotech; column volume, 22 ml) which has been equilibrated with buffer A at a flow rate of 3 ml/min. The column is washed with 200 ml of buffer A. The column is then developed with a gradient of 0-10 mM maltose in 150 ml of buffer A. The retention volume of MalE/IspH fusion protein is 40 ml. Fractions are combined and dialyzed overnight against 100 mM Tris hydrochloride, pH 8.0, containing 1 mM DTT. The solution is concentrated by ultrafiltration and stored at −80° C.

Example 4

Cloning and Expression of the fldA Gene of *Escherichia coli*

The fldA gene of *E. coli* (GenBank accession number AE005246) specifying flavodoxin 1 is amplified from by position 7191 to 7721 by PCR using chromosomal *E. coil* DNA as template and the oligonucleotides fldAvo and fldAhi (Table 1) as primers. The amplificate is purified, treated with the restriction enzymes BamHI and PstI, and ligated into the expression vector pQE30 (Qiagen, Hilden, Germany) which has been treated with the same enzymes. The resulting plasmid pQEfldA is electrotransformed into *E. coli* strain XL1-Blue (Stratagene, Bullock et al., 1978) affording the recombinant strain XL1-pQEfldA.

Example 5

Cloning and Expression of the fpr Gene of *Escherichia coil*

The fpr gene of *E. coil* (GenBank accession number AE005623) specifying ferredoxin (flavodoxin):NADP$^+$ oxidoreductase is amplified from by position 5082 to 5828 by PCR using chromosomal *E. coil* DNA as template and the oligonucleotides fprvo and fprhi (Table 1) as primers. The amplificate is purified, treated with the restriction enzymes BamHI and PstI, and ligated into the expression vector pQE30 (Qiagen, Hilden, Germany) which has been treated with the same enzymes. The resulting plasmid pQEfpr is electrotransformed into *E. coli* strain XL1-Blue affording the recombinant strain XL1pQEfpr.

Example 6

Purification of Recombinant Flavodoxin (FIdA Protein)

The recombinant *E. coli* strain XL1-pQEfldA is grown in Luria-Bertani broth containing ampicillin (180 mg/l) and riboflavin (1 mg/l). Cultures are incubated at 37° C. with shaking. At an optical density (600 nm) of 0.7, IPTG is added to a final concentration of 2 mM, and the culture is incubated for 5 h. The cells are harvested by centrifugation, washed with 100 mM Tris hydrochloride, pH 8.0, and stored at −20° C.

Frozen cell mass (8 g) is thawed in 40 ml of 100 mM Tris hydrochloride, pH 8.0, containing 0.5 M sodium chloride and 20 mM imidazole hydrochloride. The suspension is subjected to ultrasonic treatment and centrifuged. The supernatant is applied to a column of Ni-chelating Sepharose FF (2.0×2 cm, Amersham Pharmacia Biotech) which has been equilibrated with 100 mM Tris hydrochloride, pH 8.0, containing 0.5 M sodium chloride and 20 mM imidazole (flow rate, 2 ml/min). The column is washed with 50 ml of 100 mM Tris hydrochloride, pH 8.0, containing 0.5 M sodium chloride and 20 mM imidazole and is then developed with a gradient of 20-100 mM imidazole in 20 ml of 100 mM Tris hydrochloride, pH 8.0, followed by a gradient of 100-500 mM imidazole in 100 mM Tris hydrochloride, pH 8.0, containing 0.5 M sodium chloride (total volume, 120 ml). Fractions containing flavodoxin are combined, concentrated by ultrafiltration and dialyzed overnight against 100 mM Tris hydrochloride, pH 8.0, containing 5 mM DTT and 0.02% sodium azide.

Example 7

Purification of Recombinant Flavodoxin Reductase (Fpr Protein)

The recombinant *E. coli* strain XL1-pQEfpr is grown in Luria-Bertani broth containing ampicillin (180 mg/l) and riboflavin (1 mg/l). Cultures are incubated at 37° C. with shaking. At an optical density (600 nm) of 0.7, IPTG was added to a final concentration of 2 mM, and the culture is incubated for 5 h. The cells are harvested by centrifugation, washed with 100 mM Tris hydrochloride, pH 8.0, and stored at −20° C.

Frozen cell mass (8 g) is thawed in 40 ml of 100 mM Tris hydrochloride, pH 8.0, containing 0.5 M sodium chloride and 20 mM imidazole hydrochloride. The suspension is subjected to ultrasonic treatment and centrifuged. The supernatant is applied to a column of Ni-chelating Sepharose FF (2.0×2 cm, Amersham Pharmacia Biotech) which has been equilibrated with 100 mM Tris hydrochloride, pH 8.0, containing 0.5 M sodium chloride and 20 mM imidazole (flow rate, 2 ml/min). The column is washed with 50 ml of 100 mM Tris hydrochloride, pH 8.0, containing 0.5 M sodium chloride and 20 mM imidazole and is then developed with a gradient of 20-100 mM imidazole in 20 ml of 100 mM Tris-hydrochloride, pH 8.0, followed by a gradient of 100-500 mM imidazole in 100 mM Tris hydrochloride, pH 8.0, containing 0.5 M sodium chloride (total volume, 120 ml). Fractions containing ferredoxin (flavodoxin):NADP+ oxidoreductase are combined, concentrated by ultrafiltration and dialyzed overnight against 100 mM Tris hydrochloride, pH 8.0, containing 5 mM DTT and 0.02% sodium azide.

Example 8

Radiochemical Assays of 1-hydroxy-2-methyl-2-(E)-butenyl 4-diphosphate reductase (IspH Protein) Activity Assay mixtures contain 50 mM Tris hydrochloride, pH 8.0, 2 mM DTT, 5.3 µM [1-$^3$H]-1-hydroxy-2-methyl-(E)-butenyl 4-diphosphate (86 µCi/µmol), 2 mM NADPH, 54 µg of flavodoxin (FldA protein), 45 µg of flavodoxin reductase (Fpr protein), and 50 µg of MalE/IspH fusion protein in a volume of 150 µl. The mixture is incubated at 37° C. for 1 h under aerobic conditions. The reaction is terminated by addition of 10 µl of 30% (w/v) trichloroacetic acid followed by immediate neutralization with 20 µl of 1 M sodium hydroxide. The mixtures are centrifuged and the supernatants are analyzed by reversed-phase HPLC using a Luna C8 column (5 µm, 4×250 mm, Phenomenex). The column is developed with 10 ml of 3% (v/v) methanol in 10 mM tetra-n-butylammonium phosphate, pH 6.0 followed by a linear gradient of 2 ml of 3-21% (v/v) methanol in 10 mM tetra-n-butylammonium phosphate, pH 6.0, a linear gradient of 13 ml of 21-35% (v/v) methanol in 10 mM tetra-n-butylammonium phosphate, pH 6.0, a linear gradient of 10 ml of 35-49% (v/v) methanol in 10 mM tetra-n-butylammonium phosphate, pH 6.0 and a linear gradient of 5 ml of 49-56% (v/v) methanol in 10 mM tetra-n-butylammonium phosphate, pH 6.0, at a flow rate of 1 ml/min. The effluent is monitored by online liquid scintillation analysis (Beta-RAM, Biostep GmbH, Jahnsdorf, Germany). The retention volumes of 1-hydroxy-2-methyl-(E)-butenyl 4-diphosphate 6 is 25 ml. IPP (7) and DMAPP (8) are both eluted at a retention volume of 36 ml.

Example 9

Photometric Assay of 1-hydrox-2-methyl-2-(E)-butenyl 4diphosphate Reductase (IspH Protein) Activity Assay mixtures contain 50 mM Tris hydrochloride, pH 8.0, 0.5 mM DTT, 0.4 mM NADPH, 0.2 mM 1-hydroxy-2-methyl-2-(E)-butenyl 4-diphosphate, 100 pg flavodoxin, 80 µg flavodoxin reductase and 50 µg IspH protein in a total volume of 1 ml. The mixtures are incubated at 37° C. The oxidation of NADPH is monitored photometrically at 340 nm. Alternatively the concentration of NADPH is determined by measuring the relative fluorescence of NADPH at 340 nm excitation/460 nm emission.

Example 10

Radiochemical Assays of 1-hydroxy-2-methyl-2-(E)-butenyl 4diphosphate Reductase Activity All steps are carried out under anaerobic conditions. Assay mixtures contain 50 mM Tris hydrochloride, pH 8.0, 7.5 mM DTT, 1.5 mM CoCl$_2$, 5.3 µM [1-$^3$H]-1-hydroxy-2-methyl-2-(E)-butenyl 4-diphosphate (86 µCi µmol$^{-1}$) and protein in a volume of 200 µl. A solution (20 µl) of 2.6 mM 10-methyl-5-deazaisoalloxazine in dimethylsulfoxide is added, and the mixture is irradiated with a W mercury pressure lamp which is placed at a distance of 15 cm. During irradiation, the sample is cooled on ice. The reaction is terminated by adding 30% (g/v) trichloracetic acid followed by immediate neutralization with 1 M sodium hydroxide. The assay mixtures are centrifuged. The supernatants are subjected to ultrafiltration (nanosep 100 kDa, Pall Gelman) and analyzed by reversed-phase ion-pair HPLC using a Luna C8 column (4×250 mm, 5 µm, Phenomenex) which is developed with 15 ml of 10 mM tetra-n-butylammonium phosphate, pH 6.0 followed by a linear gradient of 45 ml of 0-42% (v/v) methanol in 10 mM tetra-n-butylammonium phosphate, pH 6.0, at a flow rate of 0.75 ml min$^{-1}$. The effluent is monitored by online liquid scintillation analysis (Beta-RAM, Biostep GmbH, Jahnsdorf, Germany). The retention volume of 6 is 48 ml. IPP (7) and DMAPP (8) are both eluted at a retention volume of 66 ml. This assay is repeated in the presence of a sample to be tested for inhibition of said enzymatic conversion.

TABLE 1

Oligonucleotides used herein.

Designation 5'-Sequence-3'

| | |
|---|---|
| lytBvo | TGGAGGGGATCCATGCAGATCCTGTTGGCCACC (SEQ ID NO: 1) |
| lytBhi | GCATTTCTGCAGAACTTAGGC (SEQ ID NO: 2) |
| fldAvo | GTCAGTGGATCCATGGCTATCACTGGCATCTTTTCG (SEQ ID NO: 3) |
| fldAhi | GGAGCTCTGCAGTCAGGCATTGAGAATTTCG (SEQ ID NO: 4) |
| fprvo | GGTCTGGGATCCATGGCTGATTGGGTAACAGGC (SEQ ID NO: 5) |
| fprhi | GTTCAGCTGCAGTTACCAGTAATGCTCCGC (SEQ ID NO: 6) |

REFERENCES

1. Bach, T. J. (1995) *Lipids* 30, 191-202.
2. Bloch, K. (1992) *Steroids* 57, 378-382.
3. Bochar, D. A., Friesen, J. A., Stauffacher, C. V. & Rodwell, V. W. (1999) *Comprehensive natural product chemistry*, ed. Cane, D. (Pergamon, Oxford) Vol. 2, pp. 15-44.
4. Qureshi, N. & Porter, J. W. (1981) *Biosynthesis of isoprenoid compounds*, eds. Porter, J. W. & Spurgeon, S. L. (John Wiley, New York) Vol. 1, pp. 47-94.
5. Schwarz, M. & Arigoni, D. (1999) *Comprehensive natural product chemistry*, ed. Cane, D. (Pergamon, Oxford) Vol. 2, pp. 367-399.
6. Rohmer, M. (1999) *Comprehensive natural product chemistry*, ed. Cane, D. (Pergamon, Oxford) Vol. 2, pp. 45-68.
7. Eisenreich, W., Schwarz, M., Cartayade, A., Arigoni, D., Zenk, M. H. & Bacher, A. (1998) *Chem. Biol.* 5, R221-R233.
8. Sprenger, G. A., Schörken, U., Wiegert, T., Grolle, S., deGraaf, A. A., Taylor, S. V., Begley, T. P., Bringer-Meyer, S. & Sahm, H. (1997) *Proc. Natl. Acad. Sci. U.S.A.* 94, 12857-12862.
9. Lois, L. M., Campos, N., Putra, S. R., Danielsen, K., Rohmer, M. & Boronat, A. (1998) *Proc. Natl. Acad. Sci. U.S.A.* 95, 2105-2110.
10. Takahashi, S., Kuzuyama, T., Watanabe, H. & Seto, H. (1998) *Proc. Natl. Acad. Sci. U.S.A.* 95, 9879-9884.
11. Rohdich, F. Wungsintaweekul, J., Fellermeier, M., Sagner, S., Herz, S., Kis, K., Eisenreich, W., Bacher, A. & Zenk, M. H. (1999) *Proc. Natl. Acad. Sci. U.S.A.* 96, 11758-11763.
12. Lüttgen, H., Rohdich, F., Herz, S., Wungsintaweekul, J., Hecht, S., Schuhr, C. A., Fellermeier, M., Sagner, S., Zenk, M. H., Bacher, A. & Eisenreich, W. (2000) *Proc. Natl. Acad. Sci U.S.A.* 97, 1062-1067.
13. Herz, S., Wungsintaweekul, J., Schuhr, C. A., Hecht, S., Lüttgen, H., Sagner, S. Fellermeier, M., Eisenreich, W., Zenk, M. H., Bacher, A. & Rohdich, F. (2000) *Proc. Natl. Acad. Sci. U.S.A.* 97, 2486-2490.
14. Rohdich, F., Kis, K., Bacher, A. & Eisenreich, W. (2001) *Curr. Opin. Chem. Biol.* 5, 535-540.
15. Hecht, S., Elsenreich, W., Adam, P., Amslinger, S., Kis, K., Bacher, A., Arigoni, D. & Rohdich, F. (2001) *Proc. Natl. Acad. Sci. U.S.A.* 98,14837-14842.
16. Altincicek, B., Kollas, A., Eberi, M., Wiesner, J., Sanderbrand, S., Hintz, M., Beck, F. & Jomaa, H. (2001) *FEBS Lett.* 499, 37-40.
17. Wolff, M., Seemann, M., Grosdemange-Billiard, C., Tritsch, D., Campos, N., Rodriguez-Concepcion, M., Boronat, A., Rohmer, M. (2002) *Tetrahedron Lett.* 43, 2555-2559.
18. Rohdich, F., Hecht, S., Gärtner, K., Adam, P., Krieger, C., Amslinger, S., Arigoni, D., Bacher, A. & Eisenreich, W. (2002) *Proc. Natl. Acad. Sci. U.S.A.* 99, 1158-63.
19. Adam, P., Hecht, S., Eisenreich, W., Kaiser, J., Gräwert, T., Arigoni, D., Bacher, A. & Rohdich, F. (2002) *Proc. Natl. Acad. Sci. U.S.A.* 99, 12108-12113.
20. Hecht, S., Amslinger, S., Jauch, J., Kis, K., Trentinaglia, V., Adam, P., Eisenreich, W., Bacher, A. & Rohdich, F. (2002) *Tetrahedron Lett.* 43, 8929-8933.
21. Studier, F. W., Rosenberg, A. H., Dunn, J. J. & Dubendorf, J. W. (1990) *Methods Enzymology* 185, 60-89.
22. Sambrook, J., Fritsch, E. F. & Maniats, T. (1983) *Molecular cloning: A Laboratory Manual*, 2$^{nd}$ Ed., Cold Spring Harbor Laboratory, Cold Spring Harbor, N.Y.

The invention claimed is:

1. An assay for testing a sample for the presence or absence of inhibition of the enzymatic conversion of 1-hydroxy-2-methyl-(E)-butenyl 4-diphosphate into isopentenyl diphosphate and/or dimethylallyl diphosphate comprising the following steps:
   (a) reacting an aqueous mixture containing 1-hydroxy-2-methyl-(E)-butenyl 4-diphosphate, a 1-hydroxy-2-methyl-(E)-butenyl 4-diphosphate reductase, NAD(P)H, flavodoxin, and a flavodoxin reductase under predetermined reaction conditions for a predetermined period of time;
   (b) analyzing the reaction mixture obtained in step (a) for the consumed amount of 1-hydroxy-2-methyl-(E)-butenyl 4-diphosphate and/or NAD(P)H and/or for the produced amount of isopentenyl diphosphate, and/or dimethylallyl diphosphate and/or NAD(P)$^+$;
   (c) repeating step (a) in the presence of the sample to he tested;
   (d) repeating step (b) with the reaction mixture defined in step (e);
   (e) comparing the results of steps (b) and (d).

2. The assay according to claim 1, wherein the consumed amount of NAD(P)H is measured photometrically.

3. The assay according to claim 1, whereby in steps (b) or (d) the produced amount of NAD(P)$^+$ or isopentenyl disphosphate and/or dimethylallyl disphosplate is tested.

4. The assay according to claim 3, wherein the produced amount of NAD(P)$^+$ is measured photometrically.

5. The assay according to claim 1, wherein NADPH is used as said NAD(P)H.

6. The assay according to claim 1, wherein after the predetermined period of time the reaction is stopped by addition of trichloroacetic acid.

7. The assay according to claim 1, wherein steps (a) and (c) are carried out at 37° C. for 1 hour under aerobic conditions.

8. The assay according to claim 1, wherein steps (a) and (c) are carried out under anaerobic conditions.

9. The assay according to claim 1, wherein said 1-hydroxy-2-methyl-(E)-butenyl 4-diphosphate reductase is IspH.

10. An aqueous mixture comprising 1-hydroxy-2-methyl-(E)-butenyl 4-diphosphate reductase and a flavodoxin.

* * * * *

UNITED STATES PATENT AND TRADEMARK OFFICE
CERTIFICATE OF CORRECTION

PATENT NO. : 7,402,408 B2 Page 1 of 1
APPLICATION NO. : 10/543076
DATED : July 22, 2008
INVENTOR(S) : Adelbert Bacher et al.

It is certified that error appears in the above-identified patent and that said Letters Patent is hereby corrected as shown below:

In the Claims:

In Claim 1, in column 11, on line 62, "(c) repeating step (a) in the presence of the sample to he" should read -- (c) repeating step (a) in the presence of the sample to be --.

In Claim 1, in column 11, on line 65, "step (e);" should read -- step (c); --.

Signed and Sealed this

Twenty-first Day of October, 2008

JON W. DUDAS
*Director of the United States Patent and Trademark Office*